(12) United States Patent
Kaneko et al.

(10) Patent No.: US 6,258,901 B1
(45) Date of Patent: Jul. 10, 2001

(54) PROCESS FOR PRODUCING LIGHTLY COLORED P-VINYLPHENOL POLYMER

(75) Inventors: Masao Kaneko, Misato; Tadashi Matsumoto, Ohmiya; Nobuyuki Oka; Kunishige Ohtsu, both of Ichihara, all of (JP)

(73) Assignee: Maruzen Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/601,687

(22) PCT Filed: Jan. 28, 1999

(86) PCT No.: PCT/JP99/00360

§ 371 Date: Aug. 7, 2000

§ 102(e) Date: Aug. 7, 2000

(87) PCT Pub. No.: WO99/40132

PCT Pub. Date: Aug. 12, 1999

(30) Foreign Application Priority Data

Feb. 9, 1998 (JP) .................................................. 10-042821

(51) Int. Cl.$^7$ .............................. C08K 12/24; C07C 37/74
(52) U.S. Cl. ............................ 526/77; 526/216; 526/225; 526/237; 526/219; 526/219.6; 526/313; 568/749; 568/750; 568/756
(58) Field of Search ............................. 526/77, 216, 219, 526/219.6, 225, 237, 313; 568/749, 756, 750

(56) References Cited

U.S. PATENT DOCUMENTS 4,101,590 * 7/1978 Sato et al. ..................... 568/756 X
4,517,349 * 5/1985 Fujiwara et al. ..................... 526/313

OTHER PUBLICATIONS

JP, 51-39788, A, Maruzen Petrochemical Co., Ltd) Apr. 2, 1976 JP, 57-30127 B.
JP, 61-291606, A (Maruzen Petrochemical Co., Ltd.) Dec. 22, 1986 JP, 3-39528, B.
JP, 63-130604, A (Maruzen Petrochemical Co., Ltd.) Jun. 2, 1988.
JP, 51-105389, A (Kenji Kanesaki) Sep. 17, 1976.

* cited by examiner

Primary Examiner—Fred Teskin
(74) Attorney, Agent, or Firm—Melvin I. Stoltz

(57) ABSTRACT

There is provided a process for efficiently and economically producing a polymer which is superior in transmittances of visible light and far-ultraviolet light, has a high molecular weight and is light-colored. A process for producing a light-colored vinylphenol-based polymer by subjecting p-vinylphenol to homopolymerization or subjecting p-vinylphenol and a vinyl compound copolymerizable with p-vinylphenol to copolymerization, in the presence of a cationic polymerization catalyst or a radical polymerization initiator, which process comprises subjecting a p-vinylphenol-containing raw material to vacuum flash distillation in the presence of a phenolic compound having no unsaturated side chain and water and subjecting the resulting p-vinylphenol-containing fraction to polymerization.

9 Claims, No Drawings

US 6,258,901 B1

PROCESS FOR PRODUCING LIGHTLY COLORED P-VINYLPHENOL POLYMER

TECHNICAL FIELD

The present invention relates to a process for producing a light-colored p-vinylphenol-based polymer. More particularly, the present invention relates to a process for producing, in simple steps, a p-vinylphenol-based polymer which is superior in transmittance of far-ultraviolet light, has a high molecular weight and is light-colored.

BACKGROUND ART p-Vinylphenol-based polymers are in use in various industrial fields, as functionalized polymer materials such as photosensitive resin, thermosetting resin, coating material, material for rust preventive, and the like. When an ordinary unpurified p-vinylphenol monomer is used as a polymerization raw material, however, the obtained polymer (p-vinylphenol-based polymer) has a yellowish brown color and has had limited applications.

Further, in recent years, p-vinylphenol-based polymers have drawn attention as a substance essential for use in a photoresist for production of super integrated semiconductor circuit, in the field of photosensitive electronic materials. In order to use a p-vinylphenol-based polymer in this photoresist application, the solution of the polymer is required to be superior in transmittances of visible light and far-ultraviolet light (KrF excimer laser beam of 248 nm) as well as in heat resistance. The heat resistance of a p-vinylphenol-based polymer can be evaluated by, for example, glass transition temperature; in order for the polymer to have excellent heat resistance, the polymer is required to have a molecular weight not lower than a certain high value, specifically a weight-average molecular weight of about 7,000 or higher. Incidentally, this specific value of molecular weight differs depending upon the kind of the polymer.

As to the process for production of p-vinylphenol-based polymer, various processes are known and they can be largely divided into two kinds of processes.

The first process comprises subjecting a p-vinylphenol monomer which is obtained by hydrolysis of acetoxystyrene, decarboxylation of hydroxycinnamic acid, catalytic decomposition of bisphenolethane, dehydrogenation of ethylphenol or the like, to homopolymerization or copolymerization in the presence of a radical polymerization initiator or a cationic polymerization catalyst. The second process comprises subjecting a monomer which is obtained by protecting the hydroxyl group of p-vinylphenol with an acetyl group, a trialkylsilyl group, a tert-butyl group, a tert-butoxycarbonyl group or the like, to homopolymerization or copolymerization in the presence of a radical polymerization initiator or an anionic polymerization catalyst and then removing the protective group for reversion to hydroxyl group.

Since a p-vinylphenol monomer is used as a polymerization raw material, the first process has a merit of being able to obtain an intended p-vinylphenol polymer directly. However, the p-vinylphenol-containing reaction mixture obtained in the synthesis of p-vinylphenol monomer contains impurities considered to hinder the formation of polymer, as part of coloring-causing substances; therefore, in the cationic polymerization of p-vinylphenol monomer, it becomes necessary to purify the p-vinylphenol monomer which is a polymerization material. However, since p-vinylphenol is very unstable thermally and causes polymerization easily, it is difficult to increase its purity to a high level by distillation. Hence, for example, JP-A-51-39788 discloses a method of repeating recrystallization using a hydrocarbon type solvent such as hexane or the like. This method enables production of a polymer of high molecular weight and substantially no coloring, but has not been fully satisfactory for practical application because the purification method by recrystallization is complex and brings about large loss of intended product.

As to the radical polymerization of p-vinylphenol monomer, for example, JP-A-61-291606 or JP-A-63130604 discloses a method of polymerizing a p-vinylphenol monomer in the presence of a phenol having no unsaturated side chain and water for suppression of runaway reaction. In this method, however, since the p-vinylphenol-containing reaction mixture obtained in the synthesis of p-vinylphenol monomer contains coloring-causing substances as mentioned previously, the polymer obtained from the reaction mixture per se (not subjected to any purification) is colored and has been insufficient in transmittances of visible light and far-ultraviolet light. Further, since the concentration of the raw material p-vinylphenol monomer in the reaction system is inevitably low, it has been difficult to obtain a polymer of high molecular weight.

Meanwhile, in the second process, the hydroxyl group-protected p-vinylphenol, unlike the above-mentioned p-vinylphenol monomer, is generally distillable. Therefore, the second process has a merit of being able to polymerize a high-purity monomer obtained by distillation. In the second process, however, it is necessary to remove the protective group of a formed polymer from the polymer in order to obtain an intended polymer; therefore, coloring of polymer may occur in the removal of the protective group and the post-treatment of the formed polymer increases the number of process steps, which have been the drawbacks of the second process.

The object of the present invention is to solve the above-mentioned problems of conventional processes for production of p-vinylphenol polymer and provide a process for producing a light-colored polymer superior in transmittances of visible light and far-ultraviolet light and high in molecular weight, efficiently and economically. As a target for improvement in coloring in visible light wavelength region, a transmittance of 90% can be employed because coloring is hardly noticeable at a light transmittance of higher than 90% and is easily noticeable at a light transmittance of lower than 90%.

DISCLOSURE OF THE INVENTION

In view of the above situation, the present inventors made an intensive study. As a result, the present inventors found out that in subjecting p-vinylphenol to homopolymerization or copolymerization with a vinyl compound copolymerizable with p-vinylphenol to produce a p-vinylphenol-based polymer, there can be produced, by using a raw material p-vinylphenol subjected to a distillation treatment under particular conditions, a light-colored (white to light yellow) p-vinylphenol-based polymer high in transmittances of visible light and far-ultraviolet light and also high in molecular weight. The present invention has been completed based on the above finding.

The gist of the present invention lies in a process for producing a light-colored vinylphenol-based polymer by subjecting p-vinylphenol to homopolymerization or subjecting p-vinylphenol and a vinyl compound copolymerizable with p-vinylphenol to copolymerization, in the presence of a cationic polymerization catalyst or a radical polymerization initiator, which process comprises subjecting a p-vinylphenol-containing raw material to vacuum flash distillation in the presence of a phenolic compound having no unsaturated side chain and water, and subjecting the resulting p-vinylphenol-containing fraction to polymerization.

BEST MODE FOR CARRYING OUT THE INVENTION

The present invention is described in detail below.

The light-colored p-vinylphenol-based polymer of the present invention includes a homopolymer of p-vinylphenol; a copolymer between p-vinylphenol and a vinyl compound copolymerizable with p-vinylphenol, such as m-vinylphenol, styrene or derivative thereof, acrylic acid or ester thereof, methacrylic acid or ester thereof, maleic anhydride, maleic acid or ester thereof, maleimide or the like; a benzene nucleus-substituted product of said polymer; a chemically modified polymer obtained by esterifying or etherifying the phenolic hydroxyl group moiety of said polymer; and so forth.

p-Vinylphenol, which is a polymerization raw material in the process of the present invention, can be produced by any of various known methods. The known methods include, for example, hydrolysis of acetoxystyrene, decarboxylation of hydroxycinnamic acid, catalytic decomposition of bisphenolethane and dehydrogenation of ethylphenol. The p-vinylphenol obtained by such a method may ordinarily be a reaction mixture obtained in the synthesis reaction, that is, a p-vinylphenol-containing reaction mixture per se, or a p-vinylphenol mixture obtained by removing the catalyst present in the reaction mixture. Incidentally, each of the p-vinylphenol-containing reaction mixture and the p-vinylphenol mixture is hereinafter referred to as crude p-vinylphenol.

The crude p-vinylphenol may contain, depending upon the production method used, phenolic compounds having no unsaturated side chain such as phenol, ethylphenol, cresol and the like, which are impurities formed as by-products of synthesis reaction, and water used as a reaction diluent. These impurities and water need not be separated from the crude p-vinylphenol and can be utilized as an unsaturated side chain-free phenolic compound (hereinafter abbreviated simply as phenolic compound) and water, which are required in the vacuum flash distillation of p-vinylphenol-containing raw material conducted in the practice of the present invention.

For example, the crude p-vinylphenol obtained in the dehydrogenation of p-ethylphenol, ordinarily contains phenol, ethylphenol, water, etc.; therefore, it can be used per se in vacuum flash distillation in the present invention without adding thereto a phenolic compound or water.

As mentioned previously, the crude p-vinylphenol obtained by any of various methods contains impurities which hinder the polymerization of p-vinylphenol or allow the formed p-vinylphenol polymer to have coloring or reduced light transmittance. However, since p-vinylphenol is very unstable thermally, that is, causes easy polymerization under heating and makes difficult the measurement of its boiling point, removal of impurities from the crude p-vinylphenol by ordinary distillation is difficult as mentioned previously. It has been newly found that, by subjecting a p-vinylphenol-containing raw material to vacuum flash distillation with a phenolic compound and water, the polymerization of p-vinylphenol is prevented and substantial separation and removal of impurities is possible.

That is, in the process of the present invention, by subjecting a p-vinylphenol-containing raw material to vacuum flash distillation in the presence of a phenolic compound and water, it is possible to collect, as a distillate, a p-vinylphenol for polymerization which is free from impurities (the impurities give a polymer having low light transmittance, coloring and a low molecular weight). In the vacuum flash distillation, the most parts of phenolic compound and water are distilled together with p-vinylphenol and contained in the p-vinylphenol fraction, and the impurities ordinarily remain in the high-boiling fraction.

As the phenolic compound which is allowed to co-exist in the vacuum flash distillation, there are mentioned phenol, cresol, xylenol, ethylphenol, propylphenol, butylphenol, etc. These compounds may be used singly or in combination of two or more kinds. The amount of the phenolic compound required in the vacuum flash distillation is 10 to 1,000 parts by weight, preferably 50 to 500 parts by weight per 100 parts by weight of the p-vinylphenol contained in the material to be subjected to distillation. When the amount of the phenolic compound is small, the loss of p-vinylphenol due to its polymerization is high. Meanwhile, when the amount is too large, the concentration of p-vinylphenol in the distillate is low. As a result, it makes low the efficiency of polymenization undesirably.

When the amount of the phenolic compound formed as a by-product in the synthesis of p-vinylphenol is insufficient depending upon the synthesis method used, a phenolic compound is added separately. This phenolic compound added separately needs to be free from any unsaturated side chain as well. When a phenolic compound having an unsaturated side chain is added, it is taken into a polymer formed, which deteriorates the color of the polymer or adversely affects the molecular weight and molecular structure of the polymer.

Water is fed into the distillation system. The amount of the water required in the vacuum flash distillation is 5 to 100 parts by weight, preferably 20 to 80 parts by weight per 100 parts by weight of -the p-vinylphenol contained in the material to be subjected to distillation. When the amount of the water is small, the loss of p-vinylphenol due to its thermal polymerization is large. When the amount of the water is too large, the heat efficiency during distillation is low. When the amount of the water is insufficient, water can be fed separately.

In the present invention, the vacuum flash distillation is conducted by, for example, feeding, into a distillation apparatus, a material to be subjected to distillation a which is a crude p-vinylphenol or its mixture with appropriate amounts of a phenolic compound and water, and giving rise to quick distillation of the distillation material in a state similar to simple distillation, with no refluxing, and in a residence time as short as possible. Therefore, the vacuum flash distillation is different from so-called rectification in which a distillate is refluxed for separation of intended fraction. The vacuum flash distillation of the present invention can be conducted batchwise or continuously. As the apparatus for the vacuum flash distillation, there can be mentioned, for example, a rotary evaporator and a thin film evaporator.

In the vacuum flash distillation, the heating temperature is generally kept as low as possible in order to suppress the polymerization of p-vinylphenol present in the material to be subjected to distillation. As to the degree of vacuum, there is no particular restriction; however, a vacuum degree as high as possible,. i.e. a low pressure is preferred in the practical application. The vacuum used is generally 200 mmHg or less, preferably 100 mmHg of less, more preferably 50 mmHg or less.

The temperature of the vacuum flash distillation differs naturally depending upon the degree of the vacuum used. Too low a temperature makes slow the distillation rate of p-vinylphenol; as a result, a residence time of heating of p-vinylphenol becomes long and the possibility of p-vinylphenol polymerization becomes high. Meanwhile, when the temperature is too high, the impurities to be separated are distilled together with p-vinylphenol; the effect of the vacuum flash distillation is reduced; the possibility of p-vinylphenol polymerization becomes high as well. Therefore, the temperature (still temperature) range of the vacuum flash distillation is ordinarily 100 to 300° C., preferably 120 to 250° C., more preferably 130 to 190° C.

The residence time of the material to be subjected to distillation, in the vacuum flash distillation apparatus is preferred to be as short as possible and is ordinarily within 10 minutes, preferably within 5 minutes.

The appropriate recovery of the fraction obtained in the vacuum flash distillation is ordinarily 90% by weight or less, preferably 60 to 85% by weight, because when the recovery is too high, the impurities to be separated are distilled together with p-vinylphenol, the effect of the vacuum flash distillation is low and the possibility of p-vinylphenol polymerization is high and, when the recovery is too low, the loss of p-vinylphenol is large.

In the polymerization reaction of the present invention, two methods, i.e. cationic polymerization and radical polymerization can be used. Selection of either one of the two methods is appropriately made depending upon the homopolymerization or copolymerization -of p-vinylphenol or upon the molecular weight of the polymer to be obtained. That is, in the homopolymerization of p-vinylphenol, cationic polymerization or radical polymerization is used generally; and in the copolymerization of p-vinylphenol, radical polymerization is used generally. For example, in obtaining a p-vinylphenol homopolymer having a high molecular weight of, in particular, several tens of thousands or more, cationic polymerization is used suitably.

First, in the cationic polymerization of p-vinylphenol, either one of two methods can be employed depending upon whether the polymerization temperature is relatively low or high.

The first cationic polymerization method is carried out, for example, in the presence of a cationic polymerization catalyst, with a solvent added or not added to a crude p-vinylphenol obtained by vacuum flash distillation. This polymerization method is characterized in that it is conducted at a relatively low temperature of 50° C. or lower and in a nearly non-aqueous state. Therefore, the p-vinylphenol fraction as a polymerization raw material obtained by vacuum flash distillation need be polymerized after having been dehydrated as sufficiently as possible. The dehydration is conducted by, for example, heating under vacuum using a rotary evaporator, a thin film evaporator or the like, azeotropic distillation, or use of an adsorbent. In the heating under vacuum, the water content in the p-vinylphenol fraction is reduced to about 0.1% by weight, for example, by heating the fraction to about 40° C. under a vacuum of several mmHg. In the azeotropic distillation, the water content can be reduced to a even lower level, i.e. about 0.05% by weight, for example, by adding a solvent (e.g. toluene) capable of giving rise to azeotropic distillation with water and conducting heating under vacuum. In using an adsorbent, the water content can be reduced to a further lower level, i.e. about 0.01% by weight or less by using, as an adsorbent, a molecular sieve, active alumina or the like and contacting the p-vinylphenol fraction with the adsorbent.

Since the water content in the p-vinylphenol fraction has an influence on the molecular weight of the polymer to be obtained, thorough attention need be paid to the water content while considering the polymerization method to be used. The acceptable water content differs also depending upon other reaction conditions such as reaction temperature, kinds and use amounts of catalyst and solvent, and the like.

As the polymerization catalyst, there can be used a Lewis acid such as boron trifluoride, a boron trifluoride complex, aluminum trichloride, tin tetrachloride, titanium tetrachloride, iodine or the like; and a protonic acid such as p-toluenesulfonic acid, methanesulfonic acid, trifluoromethanesulfonic acid, oxalic acid, formic acid, maleic acid, sulfuric acid, phosphoric acid or the like. Preferred as the Lewis acid among above is boron trifluoride, a boron trifluoride complex or iodine; and preferred as the protonic acid is p-toluenesulfonic acid or oxalic acid. Particularly preferred is a boron trifluoride-diethyl ether complex because it is relatively stable and easy to handle, produce a high-molecular polymer and can easily be separated from the polymer formed. Too large an amount of catalyst gives a low-molecular polymer, and too small an amount of catalyst results in low yield of polymer. Therefore, the appropriate amount of the catalyst used is generally 0.05 to 1.0 mole per 100 moles of p-vinylphenol.

When a solvent is used in the polymerization, there is used, as the solvent, a halogenated hydrocarbon solvent such as dichloromethane, carbon tetrachloride or the like; an aromatic hydrocarbon such as benzene, toluene or the like; or a nitrile such as acetonitrile, propionitrile or the like. Of these solvents, particularly preferred is a nitrile because it has excellent solubility for p-vinylphenol polymer, has a low boiling point and is easy to remove from the polymer formed. The amount of the solvent used is ordinarily 50 to 1,000 parts by weight per 100 parts by weight of the p-vinylphenol fraction obtained by vacuum flash distillation.

The polymerization temperature is an important factor affecting the molecular weight of the polymer obtained, and is generally −70 to 50° C., preferably −30 to 30° C. The polymerization time is 10 minutes to 2 hours, preferably 20 minutes to 1 hour.

By the first cationic polymerization method, a polymer having a weight-average molecular weight of about 10,000 to 100,000 is obtained. Very importantly, when a polymer having a molecular weight of about 10,000 is obtained, the polymer has a weight-average molecular weight (Mw)/ number-average molecular weight (Mn) ratio of 1.3 or less. This ratio is an indicator of molecular weight distribution, then the polymer has a very narrow molecular weight distribution.

The second cationic polymerization method is carried out at 30° C. or above which is a relatively high temperature for cationic polymerization, in a high water content state. Therefore, in this method, the p-vinylphenol fraction obtained by the vacuum flash distillation need not be dehydrated and per se can be used as a polymerization raw material. As the polymerization catalyst, there can be used any of the catalysts mentioned with respect to the first polymerization method; however, particularly suitable is an organic carboxylic acid such as oxalic acid, formic acid or maleic acid or an organic sulfonic acid such as p-toluenesulfonic acid or methanesulfonic acid. The amount of the catalyst used is 0.01 to 1.0 mole per 100 moles of p-vinylphenol. The polymerization temperature is generally 30 to 150° C., preferably 50 to 100° C. The polymerization time is 0.5 to 10 hours.

By the second cationic polymerization method, a polymer having a weight-average molecular weight of generally about 8,000 to 15,000 is obtained. Therefore, the second cationic polymerization method is suitable for production of a polymer having a lower molecular weight than in the first cationic polymerization method.

Next, description is made on the radical polymerization of p-vinylphenol. The p-vinylphenol used as a raw material may be the p-vinylphenol fraction (obtained by the above-mentioned distillation and no treatment is applied) per se, or a material obtained by subjecting said fraction to an appropriate necessary treatment. In producing a copolymer, the p-vinylphenol fraction is mixed with a monomer copolymerizable with p-vinylphenol, which is appropriate for the intended application of the copolymer produced.

As the monomer copolymerizable with p-vinylphenol, there are mentioned styrene, chlorostyrene, methoxystyrene, tert-butoxystyrene, tert-butoxycarbonyloxystyrene, vinyltoluene, m-vinylphenol, o-vinylphenol, acrylic acid or esters thereof, methacrylic acid or esters thereof, acrylonitrile, methacrylonitrile, acrylamide, methacrylamide, maleic anhydride, maleic acid or esters thereof, maleimide, etc.

No solvent is necessarily needed in the radical polymerization, either. However, a solvent may be used at need. As the solvent, there can be used, for example, acetone, methanol, ethanol, tetrahydrofuran, dioxane, toluene or acetonitrile.

As the radical polymerization initiator, there can be used benzoyl peroxide, acetyl peroxide, tert-butyl hydroperoxide, dibenzoyl disulfide, ammonium persulfate, azobisisobutyronitrile, dimethyl 2,2'-azobisisobutyrate, 2,2'-azobis(4-methoxy-2,4-valeronitrile), 2,2'-azobis(2-methylbutyronitrile), dimethyl 2,2'-azobis(2-methylpropionate) or the like. Of these, preferred is an azo type initiator such as azobisisobutyronitrile, dimethyl 2,2'-azobisisobutyrate, 2,2'-azobis(4-methoxy-2,4-valeronitrile), 2,2'-azobis(2-methylbutyronitrile), dimethyl 2,2'-azobis(2-ethylpropionate) or the like. The amount of the radical polymerization initiator used, is 0.1 to 10 parts by weight, preferably 0.5 to 5 parts by weight per 100 parts by weight of the total of p-vinylphenol and the copolymerizable monomer. The molecular weight of the polymer obtained differs depending upon the amount of the initiator used; a large amount of initiator gives a polymer of low molecular weight and a small amount of initiator gives a polymer of high molecular weight but gives a low yield. The addition of the initiator to the polymerization system may be in one portion at the start of polymerization or may be in portions during polymerization.

The polymerization temperature is ordinarily 40 to 150° C., preferably 70 to 120° C. The polymerization time is ordinarily 20 minutes to 5 hours, preferably 1 to 3 hours. By the radical polymerization method, a polymer having a weight-average molecular weight of generally 7,000 to 30,000 is obtained.

The polymerization mixture obtained by any of the above polymerization methods is washed with a polar solvent such as water or methanol, or subjected to solvent reprecipitation, thin film evaporation or the like for removal of unreacted monomer(s), water, phenolic compound, solvent, etc., whereby an intended polymer can be recovered. Of course, it is possible to obtain an intended polymer in a solution state depending upon the purpose of the obtained polymer, by simply removing part of the used solvent, etc. The polymerization mixture obtained by cationic polymerization contains an acidic substance which is the catalyst used; therefore, in order to remove it by neutralization, it is generally preferred that the polymerization mixture is treated with a basic substance such as ammonia, amine or the like.

The present invention is described below more specifically by showing Examples and Comparative Examples. However, the present invention is in no way restricted thereto.

In the Examples and the Comparative Examples, polymer properties were measured as follows.

Molecular Weight

Measured by gel permeation chromatography.

Light transmittance

Measured by spectrophotometry. Incidentally, light transmittance at a wavelength of 248 nm was taken as an indicator of transmittance of far-ultraviolet light, and light transmittance at a wavelength of 450 nm was taken as an as indicator of coloring.

Glass Transition Temperature

Measured by differential scanning colorimetry (DSC).

Copolymer Composition

Measured by $^{13}$C-NMR method.

In the following Examples and Comparative Examples, % is % by weight unless otherwise specified.

EXAMPLE 1

572 g of a light yellowish brown crude p-vinylphenol having a composition consisting of 18.3% of p-vinylphenol, 61.5% of p-ethylphenol, 1.0% of phenol, 8.7% of p-cresol and 10.5% of water, obtained by catalytic dehydrogenation of p-ethylphenol was introduced, in small portions over 1 hour, into a rotary evaporator heated at 160° C. in an oil bath, under a vacuum of 6 mmHg, and vacuum flash distillation was conducted. 477 g of a colorless transparent distillate was recovered, and its composition was 18.1% of p-vinylphenol, 65.7% of p-ethylphenol, 1.2% of phenol, 9.8% of p-cresol and 5.2% of water. To the distillate was added 350 g of toluene. The resulting mixture was introduced again to the rotary evaporator and heated at 40° C. under a vacuum of 6 mmHg to conduct azeoptropic distillation with toluene to remove water. The water content in the thus-obtained p-vinylphenol-containing fraction was 0.036%.

32.1 g of the p-vinylphenol-containing fraction as a polymerization raw material was poured into a 300-ml flask. Thereto was added 29.4 g of acetonitrile. The resulting mixture was stirred with cooling by water of room temperature. Thereto was dropwise added 1.0 ml of an acetonitrile solution of 2% of a boron trifluoride-diethyl ether complex. Then, a polymerization reaction was conducted for 30 minutes. During the period, the temperature of the reaction system was maintained at 25 to 35° C. The reaction mixture was poured into 300 ml of toluene, followed by stirring. The resulting precipitate was recovered. The precipitate was dissolved again in 50 ml of acetone. The resulting solution was poured into 300 ml of toluene to form a precipitate. This precipitate was dissolved in 50 ml of acetone. The resulting solution was poured into 300 ml of hexane for reprecipitation. The thus-purified polymer was dried under vacuum to obtain 5.6 g of a white poly(p-vinylphenol). The poly(p-vinylphenol) had a weight-average molecular weight (Mw) of 29,200, a number-average molecular weight (Mn) of 14,300, a far-ultraviolet light transmittance at a wavelength of 248 nm (sample concentration: 0.1 g per liter of ethanol solution, cell length: 1 cm) of 79.4% (the far-ultraviolet light transmittance is hereinafter abbreviated as light transmittance), a light transmittance at a wavelength of 450 nm (sample concentration. 1.0 g per liter of ethanol solution, cell length: 10 cm) of 96.1%, and a glass transition temperature of 182° C. Incidentally, the w/Mn as an indicator of molecular weight distribution was 2.04.

COMPARATIVE EXAMPLE 1

The same crude p-vinylphenol as used in Example 1 was subjected to azeotropic distillation with toluene without being subjected to vacuum flash distillation, to reduce the water content to 0.038%. A polymerization reaction was conducted in the same manner as in Example 1 except that 28.8 g of acetonitrile was added to 32.3 g of the above-obtained fraction. The reaction mixture was purified by the same reprecipitation as in Example 1, and the resulting precipitate was dried to obtain 6.5 g of a yellowish brown poly(p-vinylphenol). The polymer had a weight-average molecular weight (Mw) of 20,400, a number-average molecular weight (Mn) of 11,500, a light transmittance at a wavelength of 248 nm, of 68.0%, a light transmittance at a wavelength of 450 nm, of 83.2%, and a glass transition temperature of 177° C.

The polymer, as compared with the poly(p-vinylphenol) obtained in Example 1, was low in all of molecular weight, light transmittance and glass transition temperature.

EXAMPLE 2

610 g of a light yellowish brown crude p-vinylphenol having a composition consisting of 41.6% of p-vinylphenol, 41.2% of p-ethylphenol, 1.1% of phenol, 7.0% of p-cresol and 9.1% of water was introduced, over 1 hour, into a rotary evaporator heated at 180° C., under a vacuum of 10 mmHg, and vacuum flash distillation was conducted. 521 g of a colorless transparent distillate was recovered, and its composition was 30.4% of p-vinylphenol, 50.8% of p-ethylphenol, 1.5% of phenol, 6.8% of p-cresol and 10.5% of water. The distillate was heated at 40° C. in a rotary evaporator under a vacuum of 6 mmHg for water removal. The water content was reduced to 0.33%.

29.1 g of the thus-obtained p-vinylphenol fraction as a polymerization raw material was placed in a 300-ml flask together with 24.5 g of acetonitrile. Thereto was dropwise added 0.8 ml of an acetonitrile solution of 2% of a boron trifluoride-diethyl ether complex with stirring and with the flask being cooled. A polymerization reaction as conducted in the same manner as in Example 1, and the reaction mixture was treated in the same manner as in Example 1 to obtain 8.8 g of a white poly(p-vinylphenol).

The polymer had a Mw of 13,100, a Mn of 10,400, a light transmittance at a wavelength of 248 nm, of 76.2%, and a glass transition temperature of 184° C. The Mw/Mn as an indicator of molecular weight distribution was as small as 1.26 and the polymer had a very narrow molecular weight distribution.

EXAMPLE 3

1,536 g of a crude p-vinylphenol having a composition consisting of 41.6% of p-vinylphenol, 44.8% of p-ethylphenol, 1.0% of phenol, 3.5% of p-cresol and 9.1% of water was introduced, over 1.5 hours, into a rotary evaporator heated at 160° C., under a vacuum of 6 mmHg, and vacuum flash distillation was conducted. 1,068 g of a distillate was recovered, and its composition was 31.3% of p-vinylphenol, 53.4% of p-ethylphenol, 1.4% of phenol, 3.8% of p-cresol and 10.1% of water.

29.3 g of the above-obtained p-vinylphenol-containing fraction, 4.0 g of m-vinylphenol having a purity of 42.0% (the remainder was m-ethylphenol), and 0.50 g of azobisisobutyronitrile as an initiator were sequentially placed in a 100-ml flask provided with a reflux condenser, and polymerized at 100° C. for 3 hours. The reaction mixture was treated in the same manner as in Example 1 to obtain 7.3 g of a white p-vinylphenol copolymer.

The copolymer had an Mw of 7,360, an Mn of 5,150, a copolymer composition of 82 (p-vinylphenol)/18(m-vinylphenol) in terms of molar ratio, a light transmittance at 248 nm, of 74.1% and a glass transition temperature of 162° C.

COMPARATIVE EXAMPLE 2

22.4 g of the same crude p-vinylphenol as used in Example 3 was mixed, without being subjected to vacuum flash distillation, with 4.0 g of m-vinylphenol having a purity of 42.0% and 0.40 g of azobisisobutyronitrile. A polymerization reaction was conducted in the same manner as in Example 3. The reaction mixture was treated in the same manner as in Example 1 to obtain 7.7 g of a yellowish brown m-vinylphenol copolymer.

The copolymer had an Mw of 5,700, an Mn of 3,600, a copolymer composition of 83 (p-vinylphenol)/17(m-vinylphenol) in terms of molar ratio, a light transmittance at 248 nm, of 66.3% and a glass transition temperature of 143° C.

EXAMPLE 4

409.8 g of a mixture consisting of 21.4% of p-vinylphenol, 59.8% of p-ethylphenol, 1.5% of phenol, 7.7% of p-cresol and 9.6% of water was introduced, over 30 minutes, into a rotary evaporator heated at 180° C. under a vacuum of 6 mmHg, and vacuum flash distillation was conducted. 364.2 g of a distillate was obtained and its composition was 21.3% of p-vinylphenol, 61.6% of p-ethylphenol, 1.5% of phenol, 7.8% of p-cresol and 7.8% of water. 132.4 g of this p-vinylphenol fraction was mixed, without being dehydrated, with 0.12 ml of a 0.5 M aqueous oxalic acid solution. The -resulting mixture was polymerized at 45° C. for 6 hours. The reaction mixture was treated in the same manner as in Example 1 to obtain 26.2 of a poly(p-vinylphenol). The polymer had a Mw of 10,470, Mn of 7,180, a light transmittance at 248 nm, of 70.5% and glass transition temperature of 173° C.

COMPARATIVE EXAMPLE 3

143.0 g of the same raw material mixture as used in Example 4 was mixed, without being subjected to vacuum flash distillation, with 0.12 ml of a 0.5 M aqueous oxalic acid solution. The resulting mixture was polymerized in the same manner as in Example 4. The reaction mixture was treated in the same manner as in Example 1 to obtain 27.2 g of a poly(p-vinylphenol). The polymer had a Mw of 9,070, a Mn of 5,800, a light transmittance at 248 nm, of 65.8% and a glass transition temperature of 142° C.

EXAMPLE 5

50.5 g of the same p-vinylphenol fraction as used in Example 1, obtained by vacuum flash distillation was placed in a 300-ml flask together with 50.5 g of acetonitrile. To the resulting mixture being stirred was dropwise added 0.3 ml of an acetonitrile solution containing 0.03 g of p-toluenesulfonic acid. A polymerization reaction was conducted for 1 hour in the same manner as in Example 1 to obtain 8.5 g of a poly(p-vinylphenol). The polymer had a Mw of 15,000, a Mn of 11,500, a light transmittance at 248 nm, of 75.5% and a light transmittance at 450 nm, of 95.4%.

EXAMPLE 6

51.0 g of the same p-vinylphenol fraction as used in Example 1, obtained by vacuum flash distillation was placed in a 300-ml flask together with 51.0 g of acetone. To the resulting mixture being stirred and cooled to 0° C. was dropwise added 1.0 ml of an acetonitrile solution containing 0.02 g of iodine. A polymerization reaction was conducted for 1 hour at 0° C. to obtain 8.3 g of a poly(p-vinylphenol). The polymer had a Mw of 13,800, a Mn of 11,200, a light transmittance at 248 nm, of 76.3% and a light transmittance at 450 nm, of 95.0%.

EXAMPLE 7

To 536.3 g of a p-vinylphenol fraction obtained by the same vacuum flash distillation as in Example 1, containing 32.9% of p-vinylphenol, 49.1% of p-ethylphenol, 1.6% of phenol, 7.0% of p-cresol and 9.4% of water were added 160.9 g of methanol as a solvent and 5.36 g of dimethyl 2,2'-azobisisobutyrate as an initiator. The resulting mixture was subjected to a polymerization reaction at 80° C. for 5 hours. The reaction mixture was treated in the same manner as in Example 1 to obtain 98.2 g of a poly(p-vinylphenol). The polymer had a Mw of 8,800, a Mn of 5,200 and a light transmittance at 248 nm, of 76.9%.

EXAMPLE 8

To 312.3 g of the same p-vinylphenol fraction as in Example 5 were added 72.1 g of methanol, 45.4 g of tert-butyl acrylate and 4.3 g of 2,2'-azobisisobutyronitrile. A polymerization reaction was conducted in the same manner as in Example 5. The reaction mixture was treated in the same manner as in Example 1 to obtain 143.2 g of a p-vinylphenol copolymer. The copolymer had a Mw of 12,600, a Mn of 7,350, a composition of 69 (p-vinylphenol)/ 31 (tert-butyl acrylate) in terms of molar ratio, and a light transmittance at a wavelength of 248 nm, of 79.8%.

EXAMPLE 9

To 500 g of a p-vinylphenol fraction obtained by the same vacuum flash distillation as in Example 1, containing 29.3% of p-vinylphenol, 52.2% of p-ethylphenol, 1.5% of phenol, 6.1% of p-cresol and 10.9% of water were added 60 g of styrene, 110 g of methanol and 3.5 g of azobisisobutyronitrile. The resulting mixture was subjected to a polymerization reaction at 80° C. for 3 hours. The reaction mixture was treated in the same manner as in Example 1 to obtain 98 g of a p-vinylphenol copolymer. The copolymer had a Mw of 10,210, a Mn of 5,970, a copolymer composition of 72 (p-vinylphenol)/28 (styrene) in terms of molar ratio, and a light transmittance at 248 nm, of 71.5%.

EXAMPLE 10

To 506.5 g of the same p-vinylphenol fraction as used in Example 5, obtained by vacuum flash distillation were added 150.3 g of methanol as a solvent and 4.4 g of 2,2'-azobis(2-methylbutyronitrile) as an initiator. A polymerization reaction was conducted at 80° C. for 3 hours to obtain 97.2 g of a poly(p-vinylphenol). The polymer had a Mw of 11,000, a Mn of 6,300, a light transmittance at 248 nm, of 75.2% and a light transmittance at 450 nm, of 95.7%.

EXAMPLE 11

To 501.8 g of the same p-vinylphenol fraction as used in Example 5, obtained by vacuum flash distillation were added 149.0 g of methanol and 4.5 g of dimethyl 2,2'-azobis (2-methylpropionate). A polymerization reaction was conducted at 100° C. for 3 hours to obtain 101.0 g of a poly(p-vinylphenol). The polymer had a Mw of 9,500, a Mn of 5,300, a light transmittance at 248 nm, of 74.0% and a light transmittance at 450 nm, of 94.8%.

INDUSTRIAL APPLICABILITY

The process of the present invention enables efficient and economical production of a light-colored p-vinylphenol-based polymer superior in transmittances of visible light and far-ultraviolet light, high in molecular weight and superior in heat resistance. The product obtained by the present process has, in general, a light transmittance at a wavelength of 248 nm, of 70% or more as measured under the conditions of a concentration of 0.1 g per liter of ethanol solution and a cell length of 1 cm, a light transmittance at a wavelength of 450 nm, of 90% more as measured under the conditions of a concentration of 1.0 g per liter of ethanol solution and a cell length of 10 cm.

What is claimed is:

1. A process for producing a light-colored vinylphenol-based polymer by subjecting p-vinylphenol to homopolymerization or subjecting p-vinylphenol and a vinyl compound copolymerizable with p-vinylphenol to copolymerization, in the presence of a cationic polymerization catalyst or a radical polymerization initiator, which process comprises subjecting a p-vinylphenol-containing raw material to vacuum flash distillation in the presence of a phenolic compound having no unsaturated side chain and water and subjecting the resulting p-vinylphenol-containing fraction to polymerization.

2. A process for producing a light-colored p-vinylphenol-based polymer according to claim 1, wherein, in the vacuum flash distillation of a p-vinylphenol-containing raw material, the phenolic compound having no unsaturated side chain and water are allowed to be present in amounts of 10 to 1,000 parts by weight and 5 to 100 parts by weight, respectively per 100 parts by weight of p-vinylphenol.

3. A process for producing a light-colored p-vinylphenol-based polymer according to claim 1, wherein the vacuum flash distillation is carried out at 100 to 300° C. under a vacuum of 200 mmHg or less.

4. A process for producing a light-colored p-vinylphenol-based polymer according to claim 1, wherein the vinyl compound copolymerizable with p-vinylphenol is m-vinylphenol, styrene, tert-butoxystyrene, acrylic acid, an acrylic acid ester, methacrylic acid or a methacrylic acid ester.

5. A process for producing a light-colored p-vinylphenol-based polymer according to claim 1, wherein the cationic polymerization catalyst is boron trifluoride, a boron trifluoride complex, iodine, p-toluenesulfonic acid or oxalic acid.

6. A process for producing a light-colored p-vinylphenol-based polymer according to claim 1, wherein the radical polymerization initiator is azobisisobutyronitrile, dimethyl 2,2'-azobisisobutyrate, 2,2'-azobis (4-methoxy-2,4-valeronitrile), 2,2'-azobis(2-methylbutyronitrile) or dimethyl 2,2-azobis 2-methylpropionate).

7. A process for producing an impurity-free p-vinylphenol as a polymerization raw material, which comprises subjecting a p-vinylphenol-containing raw material to vacuum flash distillation in the presence of a phenolic compound having no unsaturated side chain and water.

8. A process for producing an impurity-free p-vinylphenol as a polymerization raw material according to claim 7, wherein, in the vacuum flash distillation of a p-vinylphenol-containing raw material, the phenolic compound having no unsaturated side chain and water are allowed to be present in amounts of 10 to 1,000 parts by weight and 5 to 100 parts by weight, respectively per 100 parts by weight of p-vinylphenol.

9. A process for producing an impurity-free p-vinylphenol as a polymerization raw material according to claim 7, wherein the vacuum flash distillation is carried out at 100 to 300° C. under a vacuum of 200 mmHg or less.

* * * * *